United States Patent
Widrig Opalsky et al.

(10) Patent No.: US 6,750,053 B1
(45) Date of Patent: Jun. 15, 2004

(54) APPARATUS AND METHOD FOR ASSAYING COAGULATION IN FLUID SAMPLES

(75) Inventors: Cindra A. Widrig Opalsky, Ottawa (CA); David Opalsky, Ottawa (CA); Andy Maczuszenko, Toronto (CA); Imants R. Lauks, Rockcliffe Park (CA); Rhonda J. Cheadle, Ottawa (CA)

(73) Assignee: i-STAT Corporation, East Windsor, NJ (US)

( * ) Notice: Subject to any disclaimer, the term of this patent is extended or adjusted under 35 U.S.C. 154(b) by 505 days.

(21) Appl. No.: 09/712,209

(22) Filed: Nov. 15, 2000

Related U.S. Application Data

(60) Provisional application No. 60/164,935, filed on Nov. 15, 1999.

(51) Int. Cl.[7] .................................................. C12M 1/34
(52) U.S. Cl. .................... 435/287.9; 435/4; 435/13; 435/288.5; 422/68.1; 422/73; 436/69
(58) Field of Search ................................ 435/4, 13, 14, 435/18, 25, 287.1, 287.9, 288.5, 288.7; 422/57, 58, 61, 73, 68.1, 82.1, 82.02; 436/69; 204/403.04, 403.14; 205/777.5

(56) References Cited

U.S. PATENT DOCUMENTS

| | | | |
|---|---|---|---|
| 4,304,853 A | 12/1981 | Jozefonvicz et al. | |
| 4,497,744 A | 2/1985 | Fawzi | |
| 4,756,884 A | 7/1988 | Hillman et al. | |
| 4,929,426 A | 5/1990 | Bodai et al. | 422/63 |
| 5,096,669 A | 3/1992 | Lauks et al. | |
| 5,104,813 A | 4/1992 | Besemer et al. | |
| 5,200,051 A | 4/1993 | Cozzette et al. | |
| 5,208,163 A | 5/1993 | Charlton et al. | 436/63 |
| 5,302,348 A | 4/1994 | Cusack et al. | |
| 5,447,440 A | 9/1995 | Davis et al. | |
| 5,628,961 A | 5/1997 | Davis et al. | 422/63 |
| 5,798,215 A | 8/1998 | Cathey et al. | 435/7.9 |
| 5,916,522 A | 6/1999 | Boyd et al. | |
| 5,919,711 A | 7/1999 | Boyd et al. | |
| 6,060,323 A | 5/2000 | Jina | 436/63 |
| 6,130,098 A | * 10/2000 | Handique et al. | 436/180 |
| 6,143,247 A | * 11/2000 | Sheppard et al. | 422/63 |

OTHER PUBLICATIONS

Becker et al., "Prothrombin time test with chromogenic peptide substrate as thrombin indicator"; Haemostasis, 12:73, Oct. 1982.

Keith et al., "A clinical evaluation of the Hemo Tec ACT"; Proc. Am. Acad. Cardiovascular Perfusion, vol. 9, Sep. 1988:22–25.

International Search Report PCT/US00/49377, Feb. 15, 2001.

* cited by examiner

Primary Examiner—William H. Beisner
(74) Attorney, Agent, or Firm—Gilberto M. Villacorta; Robert W. Hahl; Katten Muchin Zavis Rosenman

(57) ABSTRACT

This invention is a disposable cartridge for use at the patient side to perform traditional coagulation assays on fresh whole blood or blood derivative samples. The cartridge, in use with an electronic analyzer allows a fluid sample to be metered and quantitatively mixed with reagents which activate the coagulation cascade. An artificial substrate for thrombin, the enzyme whose action results in clot formation is also provided. Clot formation is subsequently detected using a microfabricated sensor also housed within the cartridge which detects electrochemically the product of the thrombin reaction upon the synthetic substrate.

107 Claims, 9 Drawing Sheets

APPARATUS AND METHOD FOR ASSAYING COAGULATION IN FLUID SAMPLES

CROSS-REFERENCE TO RELATED APPLICATION

This application claims priority based upon my copending Provisional Application Ser. No. 60/164,935, filed Nov. 15, 1999.

FIELD OF THE INVENTION

The present invention relates to an apparatus for conducting a variety of assays that are responsive to a change in the viscosity of a sample fluid and relates to methods of conducting such assays. In particular, the present invention is related to the use of a cartridge for conducting one or more coagulation assays. The present invention makes adventitious use of a pump means for moving a fluid sample. In one embodiment, sample movement is achieved by reversibly, rapidly, and reproducibly applying pressure to a sample fluid to produce a substantially reciprocating motion that is, in turn, detectable by an appropriate sensor. The disclosed device enjoys simplicity and is adaptable to the point-of-care clinical diagnostic area, including use in accident sites, emergency rooms or medical intensive care units.

BACKGROUND OF THE INVENTION

Keeping blood in a fluid state, termed hemostasis, requires a subtle balance of pro-and anticoagulants. Procoagulants prevent excessive bleeding by blocking blood flow from a damaged vessel, whereas anticoagulants prevent clots from forming in the circulating system which could otherwise block blood vessels and lead to myocardial infarction or stroke.

The biochemical sequence leading to a blood clot is termed the coagulation cascade. The mechanism is based on catalytic conversion of fibrinogen, a soluble plasma protein, to insoluble fibrin. The enzyme catalyzing this reaction is thrombin, which does not permanently circulate in the blood in an active form but exists as prothrombin, the inactive precursor of thrombin. Conversion to thrombin occurs in the presence of calcium ions and tissue thromboplastin. This mechanism is known as the extrinsic pathway. A second, more complex, intrinsic pathway is activated by clotting factors associated with platelets and is well understood in the art.

Diagnosis of hemorrhagic conditions such as hemophilia, where one or more of the twelve blood clotting factors may be defective, can be achieved by a wide variety of coagulation tests. In addition, several tests have been developed to monitor the progress of thrombolytic therapy. Other tests have been developed to signal a prethrombolytic or hypercoagulable state, or monitor the effect of administering protamine to patients during cardiopulmonary bypass surgery. However, the main value of coagulation tests is in monitoring oral and intravenous anticoagulation therapy. Three of the key diagnostic tests are activated partial thromboplastin time (APTT), prothrombin time (PT), and activated clotting time (ACT).

An APTT test evaluates the intrinsic and common pathways of coagulation. For this reason APTT is often used to monitor intravenous heparin anticoagulation therapy. Specifically, it measures the time for a fibrin clot to form after the activating agent, calcium, and a phospholipid have been added to the citrated blood sample. Heparin administration has the effect of suppressing clot formation.

A PT test evaluates the extrinsic and common pathways of coagulation and, therefore, is used to monitor oral anticoagulation therapy. The oral anticoagulant coumadin suppresses the formation of prothrombin. Consequently, the test is based on the addition of calcium and tissue thromboplastin to the blood sample.

An ACT test evaluates the intrinsic and common pathways of coagulation. It is often used to monitor anticoagulation via heparin therapy. The ACT test is based on addition of an activator to the intrinsic pathway to fresh whole blood to which no exogenous anticoagulant has been added.

The standard laboratory technology for coagulation tests typically uses a turbidimetric method. For analysis, wholeblood samples are collected into a citrate vacutainer and then centrifuged. The assay is performed with plasma to which a sufficient excess of calcium has been added to neutralize the effect of citrate. For a PT test, tissue thromboplastin is provided as a dry reagent that is reconstituted before use. This reagent is thermally sensitive and is maintained at 4 degrees C. by the instruments. Aliquots of sample and reagent are transferred to a cuvette heated at 37 degrees C., and the measurement is made based on a change in optical density.

As an alternative to the turbidimetric method, Beker et al. (See, Haemostasis (1982) 12:73) introduced a chromogenic PT reagent (Thromboquant PT). The assay is based on the hydrolysis of p-nitroaniline from a modified peptide, Tos-Gly-Pro-Arg-pNA, by thrombin and is monitored spectrophotometrically.

Coagulation monitors are known for the analysis of whole blood. For example, a unit-use cartridge has been described in U.S. Pat. No. 4,756,884 in which dry reagents are placed into the analyzer which is then heated to 37 degrees C. before a drop of blood is introduced. The sample is mixed with the reagent by capillary draw. The detection mechanism is based on laser light passing through the sample. Blood cells moving along the flow path yield a speckled pattern specific to unclotted blood. When the blood clots, id movement ceases producing a pattern specific to clotted blood.

An automatic coagulation timer has been described which measures the activated clotting time (ACT) in blood samples from patients during cardiopulmonary bypass. The sample is added to a cartridge which incorporates a stirring device on to which the clot forms. Motion of the stirring device is controlled by a photo optical detector (See, Keeth et al., Proceedings Am. Acad. Cardiovascular Perfusion (1988) 9:22).

U.S. Pat. No. 4,304,853 discloses the use of a substrate which produces an electroactive product on reaction with the enzyme thrombin. A sensor is used to detect the electroactive product. The disclosure does not include a single-use cartridge and does not disclose the use of a second sensor to monitor the location of the sample.

U.S. Pat. No. 4,497,744 discloses a turbidometric method for assaying coagulation. Plasma containing an excess of citrate is used in the test. A reagent which induces clotting is added, the sample is placed in a turbidometer, and coagulation is indicated by an increase in the turbidity of the sample.

U.S. Pat. No. 5,096,669, incorporated herein by reference, includes the general format for use of a cartridge and analytzer for blood chemistry testing such as potassium and glucose blood levels and the use of a pump to move a sample fluid to a sensor region in a single direction.

U.S. Pat. No. 5,200,051, incorporated herein by reference, discloses efficient methods of microfabrication of sensor devices for analysis of analytes.

U.S. Pat. No. 5,302,348 discloses a blood coagulation test apparatus in which blood is forced to traverse a capillary conduit. When the time for traverse exceed the previous time by a certain percentage, coagulation is deemed to have occurred. The apparatus includes an unclosed entry port which is connected to two conduits, the first receiving the sample to be assayed, the second receiving overflow sample.

U.S. Pat. Nos. 5,447,440 and 5,628,961, both incorporated herein by reference, disclose a single-use cartridge and reader used in coagulation assays. The condition of the sample is determined by its flow properties as detected, for example, by a conductivity sensor.

U.S. Pat. Nos. 5,916,522 and 5,919,711 disclose a device which uses ion-specific electrodes to measure ionic activity of fluids including bodily fluids. The fluids are metered and transported within the device-by centrifugation and pressurization of the device.

There remains a need for the apparatus and method of conducting assays of the present invention. This invention is responsive to changes in the coagulation of a blood sample, it can be used at the point of care, especially locations, such as a doctor's office, which have no immediate access to a centralized testing facility, and the apparatus can be produced in part by microfabrication methods and is readily adapted to include a multiplicity of tests, including blood gas and analyte testing.

SUMMARY OF THE INVENTION

It has now been surprisingly discovered that the needs enumerated above, and more, can be fulfilled by the apparatus and method of the present invention. In a preferred embodiment of the invention, a disposable, single-use cartridge is disclosed which, along with an external reading device, is capable of providing information relating to the propensity of a fluid sample to undergo changes in viscosity. In particular, diagnostic data on biological fluids, can be obtained such as clotting characteristics of whole blood samples.

Most importantly, the apparatus and method disclosed can include a battery of tests, all of which can be conducted simultaneously on a single fluid sample, usually in a matter of tens of seconds. For example, the time required to perform a normal PT test is about 12 seconds, while about 300 to over 1000 seconds may be needed for ACT tests using the blood from highly heparinized patients. The apparatus and method of the present invention is preferably adapted to make use of microfabrication methods and devices, especially microfabricated electrochemical sensors, to allow optimum cartridge configuration and reproducible data acquisition, handling, processing, and storage.

Coagulation in blood or plasma occurs when fibrinogen is enzymatically converted to fibrin. In this conversion, small peptide fragments are cut from the fibrinogen molecule to produce individual fibrin strands. The strands then form a hydrogen bonded network that serves to gel the sample. The enzyme responsible for liberation of the fibrinopeptides is the protease thrombin. It is generated in its active form as the penultimate step in the "coagulation cascade", a series of sequential protease activations involving nine plasma proteins.

Thrombin is a protease that hydrolyses peptides at the carboxyl terminal of arginine. Its presence, therefore, can be determined by addition of an arginine containing substrate which, upon conversion, generates a colored, fluorescent, or electroactive species. In the broadest aspect of the invention a sensor detects the changes, for an example, an electrode in the cartridge is used to amperometrically determine the liberated electroactive species. Appearance of the electroactive species is closely correlated with coagulation of the fluid sample.

Thus, in its most general sense, one embodiment of the present invention relates to a cartridge for measuring a change in the coagulation parameters of a fluid sample comprising: (a) a housing capable of being charged with a fluid sample and equipped with a sample displacement means for applying a force against the fluid sample effective to displace at least a metered portion of the fluid sample within the housing; (b) at least one substrate, contained within the housing, capable after contact with the fluid sample of promoting enzymatic reactions related to the coagulation of the fluid sample; (c) at least one sensing means, contained within the housing, capable of detecting the enzymatic reactions in the fluid sample. In this application, the term "coagulation parameters" refers to the measurement determined by the APTT, PT, ACT and other tests generally related to clot formation, generally quantified as a time to clot formation.

In particular embodiments of the present invention the housing is equipped with one or more connecting means for engaging the housing with a reading device. For example, the cartridge may have electromechanical connectors to allow the cartridge to be engaged to an external reading device that performs a variety of functions including, but not limited to, recording, displaying, manipulating, storing or, otherwise, utilizing the measurements that can be carried out using the cartridge of the invention.

In the present invention, the cartridge is equipped with a pump for displacement of the fluid sample. For instance, the cartridge may be connected to an external pump capable of then exerting a force against the fluid sample to move the sample within the housing. Alternatively, the sample displacement means may be a pump that already forms an integral part of the cartridge. In any event, actuation of the sample displacement pump allows at least a portion of the fluid sample to move across the sensor.

In a preferred embodiment of the invention the force that is applied to the fluid sample, as well as its subsequent movement, is reversible so that at least a portion of the fluid sample is displaced back and forth across the sensing means in a substantially reciprocating manner. On contact of the fluid sample with the reagent, the subsequent changes in the thrombin content of the fluid sample are then detected by monitoring the fluid sample.

In a specific embodiment of the present invention, an apparatus is disclosed for conducting an assay that is responsive to coagulation of a fluid sample comprising: (a) at least one sensor sensitive to the displacement of a fluid sample across the sensor; (b) at least one sensor capable of detecting amperometrically an electroactive species, (c) at least one reagent capable of promoting coagulation of a fluid sample; (d) a substrate capable of reacting with an enzyme associated with coagulation with the generation of an electroactive species and (e) a pump for applying pressure against a fluid sample in the sample retainer to displace at least a portion of the fluid sample across the sensors. Preferably, the force or pressure is applied reversibly to cause the fluid sample to move in a substantially reciprocating manner, such that the fluid sample dissolves the substrate and reagent that promotes the coagulation. In particular embodiments of the present invention, a pump is provided which comprises a resilient diaphragm in fluid communication with the sample which provides a pneumatic force to the fluid sample. A preferred diaphragm pump may have an internal spring or an internal rubber sponge to promote the rapid, reproducible compression and decompression of the diaphragm.

The cartridge of this invention has provisions for receiving a blood, plasma, or other fluid sample and for precisely metering a preselected sized aliquot of the fluid sample for further processing. Such a metered aliquot is placed in contact with a premeasured amount of reagent for activating and for detecting the reactions associated with coagulation.

As mentioned previously, the present invention also provides cartridges and methods of their use in which the cartridges may be coupled to an external reading device that performs a number of functions. Hence, the present invention also relates to an apparatus in which the sensor provides a signal to an external reading device that actuates a plunger for compressing and decompressing the diaphragm pump. Where the sensor is a conductivity (conductimetric) sensor, preferably a microfabricated conductivity sensor, the signal is a conductivity output. In one embodiment, output signals below a first preselected value cause the reading device to actuate the plunger to compress the diaphragm, and output signals above a second preselected value cause the reading device to actuate the plunger to decompress the diaphragm. In addition to providing a feedback methodology, the external reading device may also provide signal processing capability in which raw data may be processed to enhance the amount of useful information that may be obtained from a given assay. The external reading device also operates an amperometric sensor which oxidizes or reduces the electrogenic species reaction product which is indicative of coagulation. This electrochemical reaction generates a current which is recorded and processed by the external reading device. Another aspect of the present invention is the maintenance of the cartridge at a given temperature, preferably at physiological temperature in order to insure a reliable and reproducible coagulation assay.

Various fluid samples may be assayed according to the present invention, including, but not limited to, biological fluids, such as whole blood and plasma. The present invention is also particularly useful for conducting assays on anticoagulated blood samples, including, but not limited to, heparinized or citrated whole blood.

It is, therefore, an object of the present invention to provide an apparatus for conducting a blood test for prothrombin time (PT) comprising: (a) at least one conductivity sensor sensitive to the displacement of a blood sample across the sensor; (b) a second sensor capable of detecting amperometrically an electroactive species; (c) at least one reagent mixture comprising thromboplastin and calcium ions; (d) a substrate capable of reacting with thrombin with the generation of an electroactive species; (e) a pump for reversibly applying pressure against the blood sample to displace at least a metered portion of the blood sample into contact with the reagent and substrate and subsequently across the sensors, preferably, in a substantially reciprocating manner, the reagent contacting and promoting the coagulation of the blood sample.

It is another object of the present invention to provide an apparatus for conducting a blood test for activated partial thromboplastin time (APTT) comprising: (a) at least one conductivity sensor sensitive to the displacement of a blood sample across the sensor; (b) a second sensor capable of detecting amperometrically an electroactive species; (c) at least one reagent mixture comprising a phospholipid and calcium ions; (d) a substrate capable of reacting with thrombin with the generation of an electroactive species; and (e) a pump for reversibly applying pressure against the blood sample to displace at least a metered portion of the blood sample into contact with the reagent and substrate and subsequently across the sensors, preferably, in a substantially reciprocating manner, the reagent contacting and promoting the coagulation of the blood sample.

It is another object of the present invention is to provide an apparatus for conducting a blood test for activated clotting time (ACT) comprises; (a) at least one conductivity sensor sensitive to the displacement of a blood sample across the sensor; (b) at least one sensor capable of detecting amperometrically an electroactive species; (c) at least one reagent capable of activating the extrinsic coagulation cascade; (d) a substrate-capable of reacting with an enzyme associated with coagulation with the generation of an electroactive species; and (e) a pump for reversibly applying pressure against the blood sample to displace at least a metered portion of the blood sample into contact with the reagent and substrate and subsequently across the sensors, preferably, in a substantially reciprocating manner, the reagent contacting and promoting the coagulation of the blood sample.

A further object of the present invention is the disclosure of a method of conducting a coagulation assay comprising: (a) placing a fluid sample in a sample retainer for retaining the fluid sample out of contact with a sensor and a reagent, the sensor sensitive to the displacement of the fluid sample across the sensor and the reagent capable of promoting a change in the viscosity of the fluid sample; (b) applying pressure against the fluid sample in the sample retainer to displace at least a portion of the fluid sample across the sensor. Preferably, the force or pressure is applied reversibly such that the fluid sample moves in a substantially reciprocating manner, such that the fluid sample contacts the reagent that promotes the viscosity change of the fluid sample; (c) detecting the displacement of the fluid sample across the sensor to indicate a change in the viscosity of the fluid sample; and (d) detecting the generation of a electroactive species.

Another object of this invention is to provide a cartridge for delivering a metered sample to an analysis location comprising: a housing having a closable sample entry port for receiving an unmetered fluid sample; a holding chamber having a first end in communication with the entry port, the holding chamber having a second end with a capillary stop; an analysis location in communication with the capillary stop, the capillary stop selectively allowing passage of a sample from the holding chamber to the analysis location; an overflow chamber in communication with the holding chamber for handling overflow of incoming sample; and a pump for providing a force to the fluid sample in the holding chamber, thereby allowing passage of the sample through the capillary stop.

Another object of the present invention is to provide a cartridge for delivering a metered fluid sample to an analysis location, comprising: a housing containing a fluid path and having first and second sides, wherein at least one side contains at least one fluid channel, said first and second sides attached with a wall located therebetween, said wall and said channels providing the fluid path; and a hydrophobic layer comprising a portion of the fluid path, the hydrophobic layer preventing flow of a fluid toward an entry port.

Another object of the present invention is to provide a cartridge adapted for use with an analyzer for assaying an enzyme in a fluid sample comprising: a housing having a sample entry port, overflow chamber, holding chamber, and analysis location, an airtight entry port closure, a pump actuated by the analyzer for moving the sample within the cartridge, one or more reagent deposits in the analysis location comprising at least one substrate capable of reaction with an enzyme in the fluid sample, the reaction of the enzyme forming a detectable reaction product, a first sensor for detecting the location of the fluid sample, and a second sensor for detecting the detectable reaction product.

Another object of the present invention is to provide a cartridge adapted for use with an analyzer for assaying an enzyme in a fluid sample comprising: a housing having a sample entry port, holding chamber, and analysis location, an airtight entry port closure, a pump actuated by the analyzer for moving the sample within the cartridge, one or more reagent deposits in the analysis location comprising at least one substrate capable of reaction with an enzyme in the fluid sample, the reaction of the enzyme forming a detectable reaction product, a hydrophobic layer comprising a portion of the analysis location, a first sensor for detecting the location of the fluid sample, and a second sensor for detecting the detectable reaction product.

Another object of the present invention is to provide a single-use cartridge used in combination with an analyzer for determining a coagulation parameter of a sample of blood or blood derivative comprising: a cartridge having an entry port for receiving an unmetered sample, an entry port closure, a holding chamber in communication at a first end with the entry port, and a capillary stop in communication with the holding chamber at a second end, the capillary stop also in communication with an analysis chamber, the holding chamber in communication with an overflow chamber for receiving and retaining excess sample, the overflow chamber in communication with a pneumatic pump actuated by the analyzer, the analyzer actuating the pneumatic pump to displace sample in the holding chamber through the capillary stop into the analysis chamber to deliver a metered portion of the sample into the analysis chamber, the analysis chamber containing a substrate for the enzyme thrombin capable of dissolving in the metered sample, an amperometric sensor for detecting the product of the reaction between thrombin and the substrate, and a conductimetric sensor for detecting the position of the sample in the analysis chamber, the amperometric sensor and the conductivity sensor connected to the analyzer for providing output signals to the analyzer, the analyzer capable of using the output signal of the conductivity sensor to actuate the pneumatic pump to control the position of the sample in the analysis chamber, the analyzer capable of determining the coagulation parameter from the output signal of the amperometric sensor, and the cartridge containing a hydrophobic region between the capillary stop and the analysis chamber to prevent sample in the analysis chamber from being drawn back into the holding chamber.

Another object of the present invention is to provide a method of assaying an enzyme in a sample of blood or blood derivative comprising the steps: obtaining a sample of blood or blood derivative, placing the sample into the entry port of a cartridge, closing the entry port, activating the pneumatic pump, thereby forcing a metered sample from the sample chamber into the analysis chamber, oscillating the sample back and forth in the analysis chamber, and determining the concentration of the reaction product using the second sensor.

Another object of the present invention is to provide a method of assaying an enzyme in a sample of blood or blood derivative comprising the steps: introducing the sample into a cartridge, metering a portion of the sample, moving the metered sample to an analysis location, mixing the metered sample with reagent at the analysis location, allowing the enzyme to react with the reagent, positioning the reacted sample at a sensor, and detecting the product of the enzyme reaction using a sensor.

The present invention further encompasses a disposable, single-use cartridge comprised of a plurality of microfabricated sensors for the determination of the presence or concentration of one or more analytes in a sample fluid, along with a microfabricated sensor for the determination of changes in the viscosity of the sample fluid as well as a microfabricated sensor for the determination of the presence of an electroactive species.

Other objects of the present invention will be evident to those of ordinary skill, particularly upon consideration of the following detailed description of the preferred embodiments.

DETAILED DESCRIPTION OF THE PREFERRED EMBODIMENTS

The following describes the invention of a disposable cartridge for use at the patient bedside to perform traditional coagulation. The cartridge provides a means by which a blood sample can be metered and quantitatively mixed with reagents that activate the coagulation cascade. Clot formation is subsequently detected using a microfabricated sensor housed within the cartridge. The functional features of the cartridge and sensor are described.

U.S. Pat. No. 5,096,669, incorporated by reference, discloses a system for near-patient testing comprised of a hand held analyzer and disposable test cartridges. The cartridge is assembled from molded components and houses the necessary reagents, calibrants, and sensors to perform a variety of clinical chemistry tests. Cartridges contain various combinations of traditional electrochemical sensors which have been miniaturized through microfabrication techniques. Lithographic processes and inventive dispensing technology are utilized to create ion selective ($Na^+$, $K^+$, $Cl^-$, $NH_3^+$, $Ca^{2+}$, pH, and $CO_2$), amperometric (glucose, creatinine, lactate, oxygen), and conductimetric (hematocrit) sensors. The sensors are packaged so that single cartridges accommodate the most common testing patterns.

BACKGROUND

Coagulation testing comprises a number of tests that are used to indicate the health of a patient s coagulation system.

Testing is used to monitor patients receiving acute or prophylactic anti-coagulation therapy or to screen the patient for coagulation abnormalities. Because the process of coagulation is complex and involves a number of blood components, several coagulation tests have been developed to probe the integrity of the various coagulation subsystems.

Figure 9:
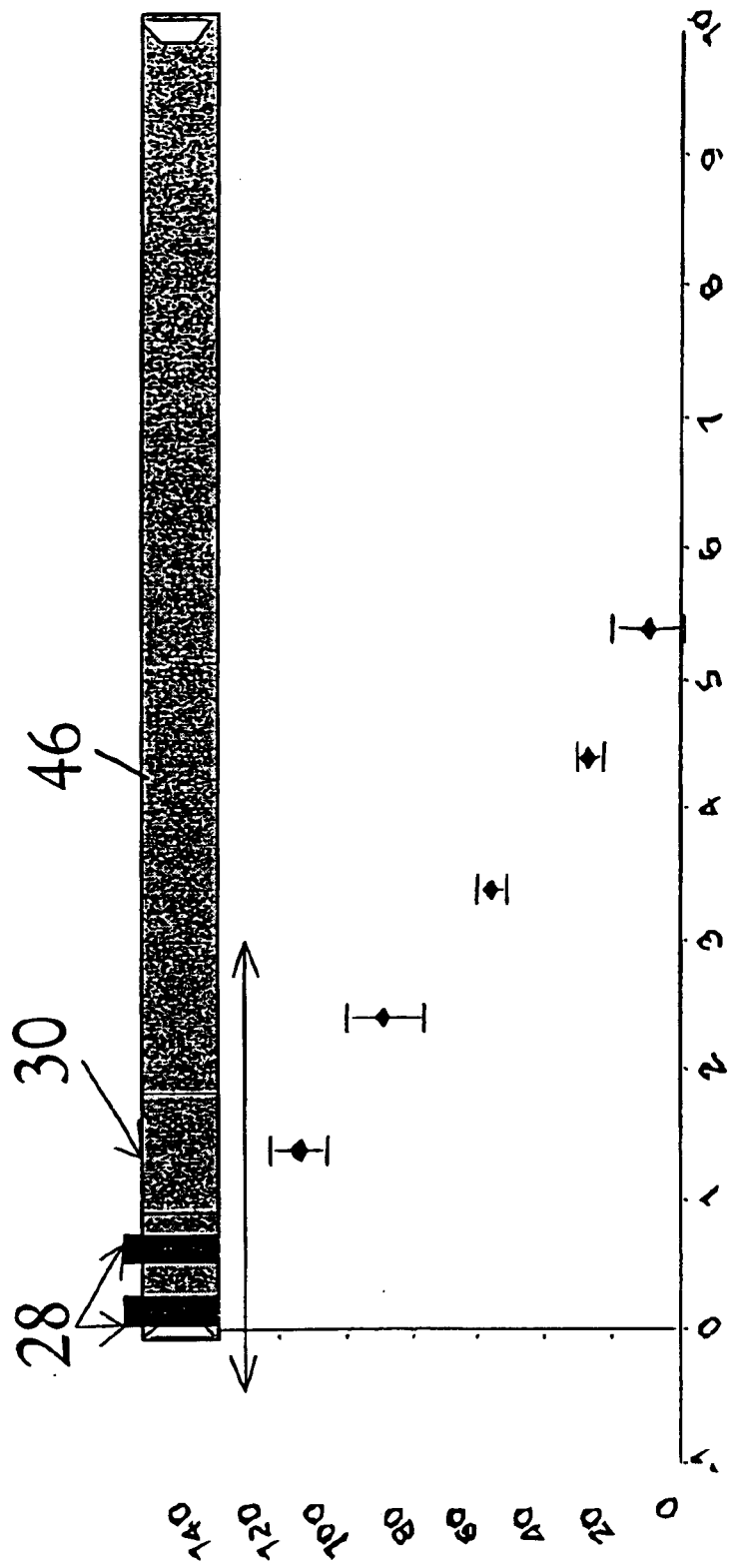
FIG. 9 is a diagram showing the concentration of reagent in the sample.

Blood clotting is the trauma-induced formation of an insoluble gelatinous plug that serves to decrease blood flow in the effected area. The gel is formed as fibrin strands, which are generated by the action of thrombin on the plasma protein fibrinogen, cross-link to form a three dimensional structure. Conversion of fibrinogen occurs as the final step in a series of enzyme reactions in which sequential coagulation enzymes, or factors, are activated. The series of enzyme reactions is called the coagulation cascade and is depicted in FIG. 9. It is initiated through the activation of Factors XII or VIII. In vivo, the former is converted to its active form at the surface of platelets that have agglomerated at sites of tissue damage. Factor VIII is activated by thromboplastin, a substance released by damaged endothelial cells. Activation of Factor XII and Factor VIII is referred to as intrinsic and extrinsic activation, respectively.

Figure 1:
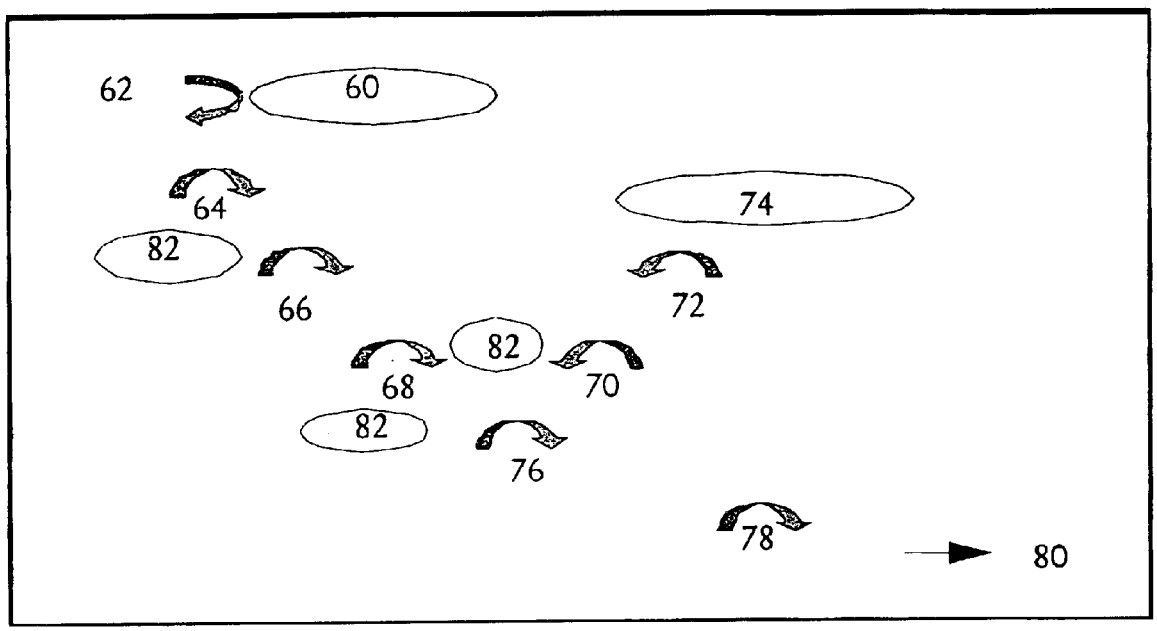
FIG. 1 is a diagrammatic representation of the coagulation cascade.

FIG. 1 is a diagrammatic representation of the enzymatic steps occurring in the coagulation cascade. Each factor is converted to its active form only during active coagulation. The arrows indicate the sequence of activations required for clot formation. As indicated, many of the reactions also require the presence of free calcium ions ($Ca^{++}$) and phospholipids (PL), jointly depicted as 82 in FIG. 1. Coagulation can be initiated through the activation of the intrinsic pathway 74 which involves the activation of Factor XII. Another way of initiating coagulation is through the extrinsic pathway 60 which causes activation of Factor XII. Activation of Factor XII is depected at 62; of Factor XI at 64; of Factor IX at 66; of Factor X at 68 and at 70; of Factor XIII at 72; of Factor II at 76 (also termed the conversion of prothrombin to thrombin); and the conversion of soluble fibrinogen to insoluble fibrin at 78 with the formation of a clot at 80.

The most frequently performed coagulation tests measure the time required for clot formation in a blood or plasma sample subsequent to the addition of activating reagents. The initiation reagent used dictates the portion of the coagulation cascade that will be activated and therefore assessed. Negatively charged surfaces mimic activation by platelets and pure tissue thromboplastin is added to initiate clotting via the intrinsic pathway. The most sophisticated laboratory instruments automatically measure, dispense, and mix reagents and sample. Less automated methods require that the user measure and mix the sample and reagent. Clot formation in these instruments is detected either mechanically or optically.

The operational specification describes the sequence of events that must occur in the course of a test cycle. For assaying an enzyme in a sample of blood or blood derivative this specification discloses the following method:
introducing the sample into a cartridge,
metering of a portion of the sample,
moving the metered sample to an analysis location,
mixing the metered sample with reagent at the analysis location,
positioning the reacted sample at a sensor, and
detecting the product of the enzyme reaction using a sensor.

The performance specification sets the criteria for parameters such as the range of results that will be reported, the necessary accuracy and precision of the test, and the acceptable operating conditions. The test results must match the sensitivity and range of the commonly accepted coagulation tests and must do so with comparable or better precision. Furthermore, as a point-of-care device may be operated by non-technically trained personnel, the analyzer software must detect any cartridge errors that do occur.

Figure 2:
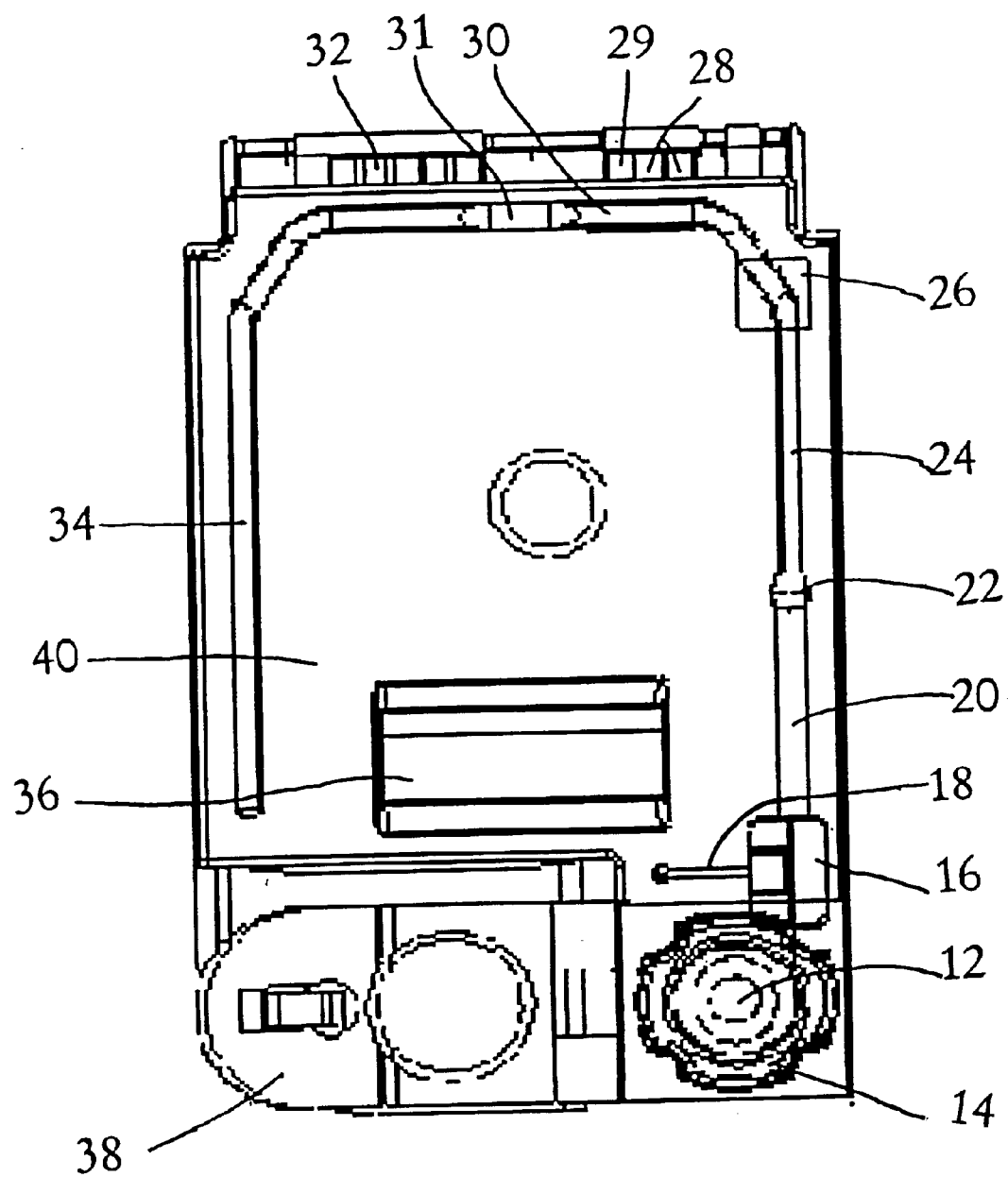
FIG. 2 is a plan view of the upper side of the cartridge.

FIG. 2 is a plan view of the top or first side 40 of the cartridge or housing 10. The sample entry port 12 is shown and it is surrounded by a circumferential excess sample well 14. A snap cover 38 closes the sample entry port 12 with the formation of an air-tight seal. A sample holding chamber 20 is in communication with the sample entry port 12. A capillary stop 22 is at the end of the sample holding chamber which is distal to the sample entry port 12. A pre-sensor channel 24 leads from the capillary stop 22 to the analysis location 31. A deposit of reagent and substrate 30 is located in the analysis location 31. In addition, in communication with the analysis location 31, there are conductimetric sensors 28, a amperometric sensor 29, and a reference sensor 32. The amperometric sensor 29 is located distal to the capillary stop 22 and the conductimetric sensors 28 are located proximal to the capillary stop 22. The analysis location 31 is in communication with the waste tube 34. A hydrophobic layer 26 is located between the pre-sensor channel 24 and the analysis location 31. The fluid path 38 consists of the sample entry port 12, the holding chamber 20, the capillary stop 22, the pre-sensor channel 24, the analysis location 31, and the waste tube 34. A flexible diaphragm pump 36 pumps air which is transmitted through the air tube 18 into the overflow chamber 16.

Although the pump in FIG. 2 is a flexible diaphragm pump, any suitable pump may be used, such as piston and cylinder, electrodynamic, and sonic.

Sample. The coagulation assays commonly performed with the cartridge of this invention use a sample of blood, or a sample of a blood derivative such as blood containing an additive or diluent, plasma, serum, or plasma or serum containing an additive or diluent Sample Introduction. The sample is deposited in the cartridge through the sample entry port 12 in FIG. 2 and shown in cross-section as 12 in FIG. 3. The opening is designed so that capillary forces will draw a hanging drop touched to the orifice of the port into the cartridge and toward the sample holding chamber. The action is a result of the geometry and high surface energy of the plastic conduit. A high surface energy is achieved with a corona treatment or equivalent treatment, such as an ion-plasma treatment, before cartridge assembly. Once blood reaches the sample holding chamber, its geometry and corona-treated surface causes the blood to pass along its length up to the point of a capillary stop. The upper limit of the cross-sectional area of the sample holding chamber is that which would prevent capillary draw if a cartridge were to be held upright as it was filled. The lower limit of the cross-section is determined by the sample volume required for testing and the reproducibility required of this volume. The sample holding chamber contains 19 microliters with a cross-sectional area of 0.0075 $cm^2$. In other embodiments the volume of the metered fluid sample is in the range of 1 microliter to 1 milliliter. A preferred volume of the metered fluid sample is in the range of 15 microliters to 50 microliters.

Metering the fluid sample. The reproducibility of the volume of sample that is moved into the sensor channel for mixing affects the reproducibility of the final concentration of dissolved reagent in the blood. The metering method described in the following provides volumetric reproducibility.

In all cartridges the metering and pumping of fluids and reagents is independent of the user. Once the user fills the cartridge, shuts the snap closure to seal the blood entry port and inserts the cartridge into the analyzer, the test cycle occurs and is monitored through the analyzer software. Upon insertion, the analyzer first recognizes the cartridge type. The appropriate test sequence is initiated and the timing, speed, and duration of all subsequent fluid motions are controlled. The blood sample is moved into the sensor channel, also termed the analysis location 31 in FIG. 2 once the heating elements stabilize at 37° C. The blood sample is moved forward as a piston in the analyzer pushes on the membrane 36 of the diaphragm pump. This forces air through the air pipe 18 that connects the air bladder and the overflow chamber 16 and moves the blood that is in front of the orifice toward the sensor channel. The volume of the metered fluid sample is the volume of the holding chamber 20 between the orifice (48 in FIG. 5) in the wall of the holding chamber and the capillary stop 22. The volume of blood that is moved will depend primarily on the volume of blood in front of the orifice and secondarily on the surface area-to-volume ratio of the sample-holding chamber, the sample hematocrit (the percent of the blood volume comprised of red blood cells), and the fluid speed. These latter three parameters determine the volume of sample that will remain on the walls of the sample holding chamber as the chamber is evacuated. The fluid will be metered most precisely at low velocity from a chamber with a low surface-area-to-volume ratio. The lower limit on the sample holding chamber cross-sectional area is determined by the allowable variation in the volume loss to shear at the necessary fluid speed.

Figure 3:
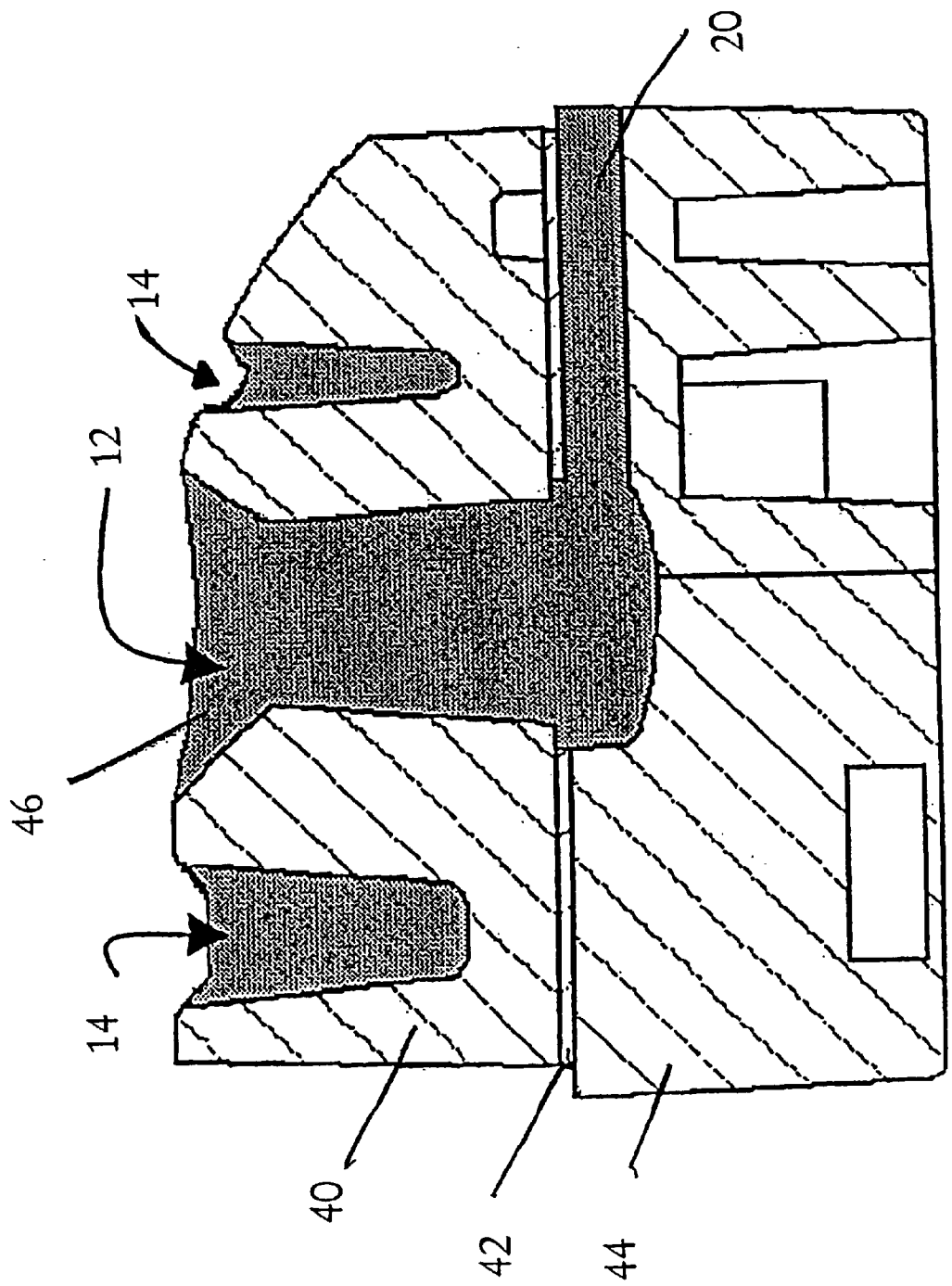
FIG. 3 is a cross-sectional view of the sample entry port area of the cartridge.

FIG. 3 is a cross-sectional view of the sample entry port 12 area of the cartridge or housing 10. FIG. 3 shows the top or first side or upper housing 40 of the cartridge, the base or second side or lower housing 44 of the cartridge, and the wall or tape or film 42 interposed between the first and second sides. The tape 42 has an adhesive layer on each side and adheres to the top 40 and base 44 sides of the cartridge. The sample entry port 12 is shown filled with sample 46, and the sample 46 has also filled the sample holding chamber 20. A circumferential well 14 surrounds the sample entry port 12 and is show filled with excess sample.

Figure 4:
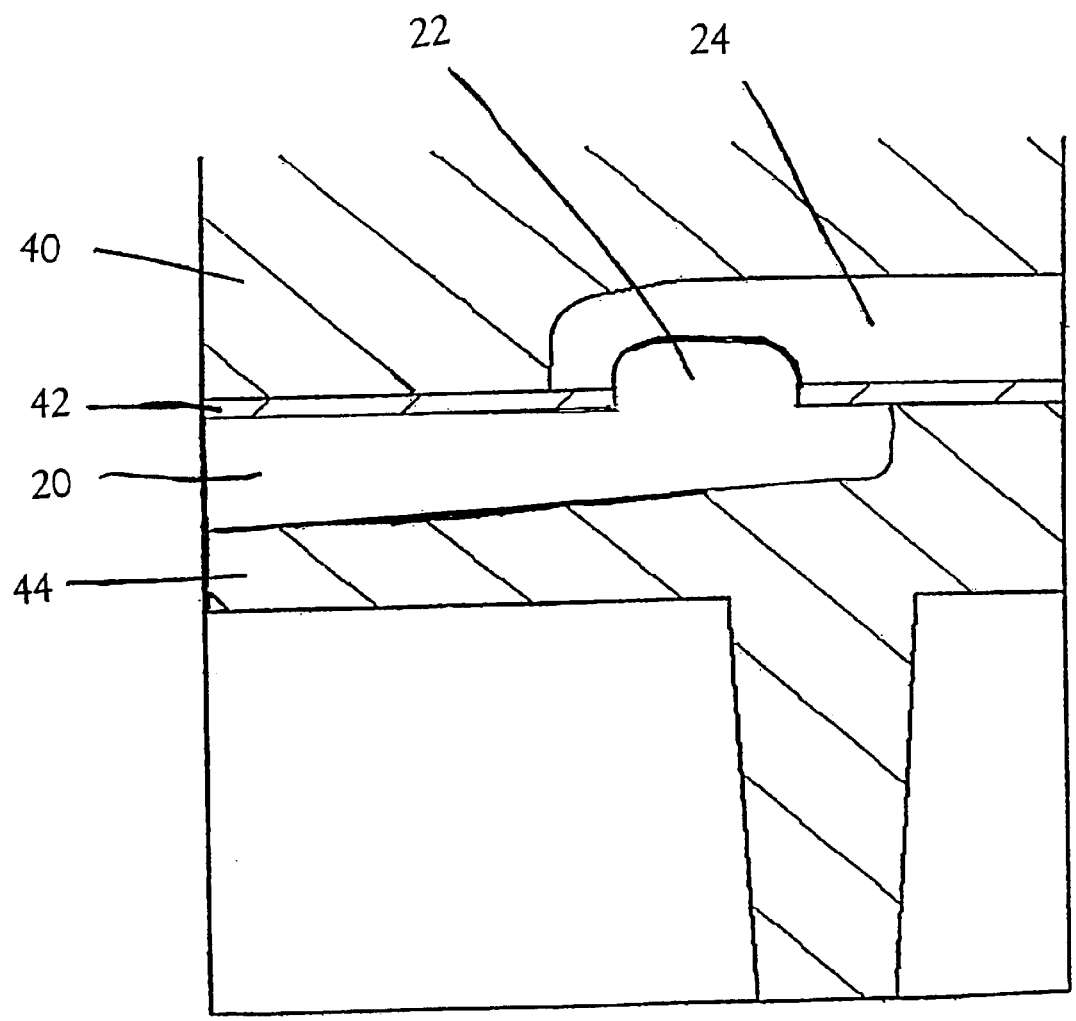
FIG. 4 is a cross-sectional view of holding chamber and pre-sensor chamber area of the cartridge.

To precisely fill the sample holding chamber, there must be sufficient capillary draw to avoid under filling the cartridge as well as a stop feature that prevents sample from overflowing into the pre-sensor channel. As depicted in FIG. 4, a capillary stop 22 is formed by a small bore or through-hole in the tape gasket 42 between overlapping sections of the sample holding chamber 20 and the pre-sensor channel 24 serves this purpose. The capillary stop 22 that is formed is relatively short; only the thickness of the tape 42 gasket. Although this decreases the resistance of the capillary and thereby decreases its effectiveness in stopping the fluid once the cartridge fills, it is necessary as it minimizes the high shear zone through which the sample must pass as it is pushed through the bore for delivery into the pre-sensor channel. The low volume high-shear region minimizes the loss of sample to the walls of the capillary and decreases the potential for the inclusion of entrapped air segments as the back end of the moving fluid column exits the capillary region.

FIG. 4 is a cross-sectional view of the conjunction of the sample holding chamber and the pre-sensor chamber 24 and the capillary stop 22. The base 44 is shown with the sample holding chamber 20 cut into it. The pre-sensor channel 24 is shown cut into the top 40. The tape 42 forms the top wall of the sample holding chamber 20 and the bottom wall of the pre-sensor chamber 24. A capillary bore or through-hole 22 pierces the tape 42 and restricts flow between the sample holding chamber 20 and the pre-sensor chamber 24.

The capillary stop of FIG. 4 is a circular bore or through-hole. Other suitable shapes for the capillary stop include rectangular and irregular in shape. If rectangular in shape, suitable examples have a smallest dimension of about 100 microns to about 400 microns. In such examples, the largest dimension of the capillary stop is about 100 microns to about 1000 microns.

Figure 5:
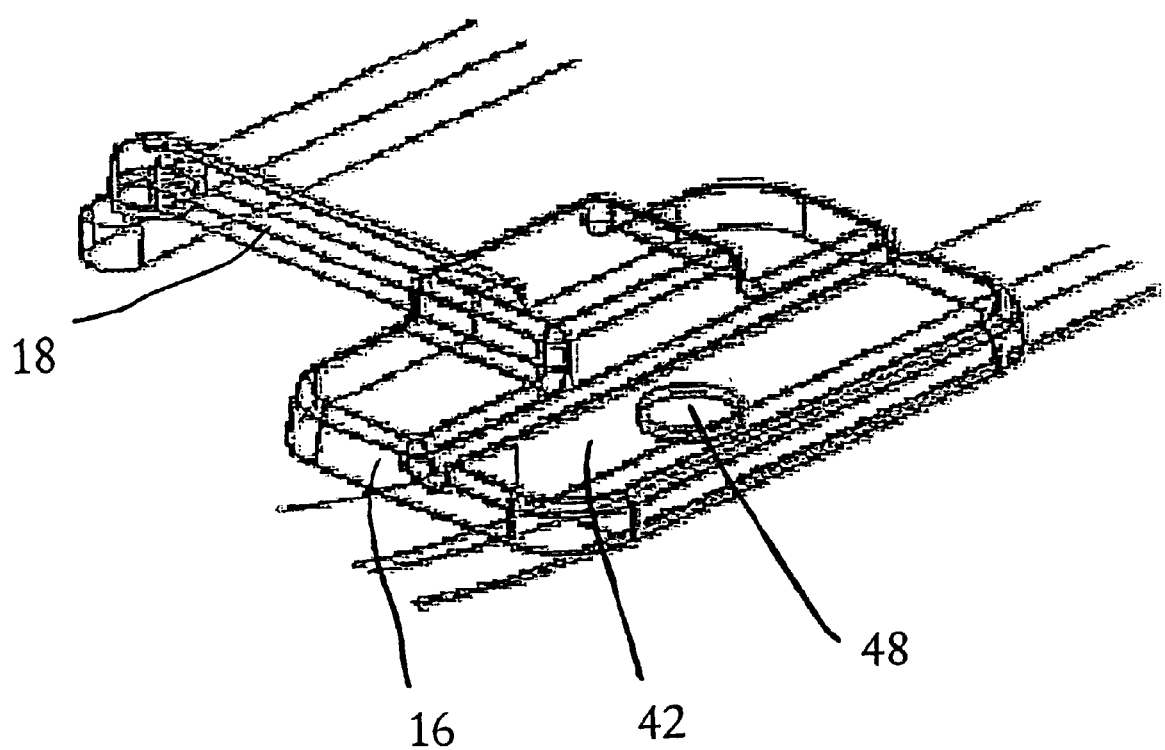
FIG. 5 is a perspective view of the overflow chamber of the cartridge.

The capillary stop is of sufficient resistance to stop capillary draw into the pre-sensor channel. It is not sufficient to resist sudden pressure changes that occur as the cartridge closure is snapped shut. To reduce the force at the capillary opening at this point, two "overflow" features are incorporated within the cartridge. The first is the overflow well 14 in FIGS. 2 and 3. As the snap closure is shut, some excess sample is pushed into the well rather than further into the cartridge. The second feature is an orifice 48 (in FIG. 5) or pressure vent through which excess sample may flow into the overflow chamber 16. As depicted in FIG. 5, the overflow chamber 16 is a low volume chamber in the cartridge top side located above the sample holding chamber and separated from the chamber by a tape 42 wall. An orifice 48 in the tape 42 allows flow of excess sample into the overflow chamber. The hole or orifice 48 in the tape gasket 42 has a greater area than the opening of the capillary stop and therefore the orifice has lower flow resistance than does the capillary stop. The overflow chamber 16 above the tape opening or orifice 48 has very low walls so that once sample is pushed through this hole, it touches the corona-treated plastic and is drawn into the to chamber. The sample displaced as the cartridge is closed is therefore trapped within this chamber. When the air bladder is compressed, air is forced through the air pipe 18 into the overflow chamber 16. The high surface area to volume ratio of this region encourages sample shear so that the air pushes a path through the excess sample leaving the excess sample on the walls of the overflow chamber.

FIG. 5 is a perspective view of the overflow chamber. 16. The overflow chamber 16 is located directly above the sample holding chamber (not shown in FIG. 4). Tape 42 which is the top wall of the sample holding chamber (20 in FIG. 2) also forms the bottom wall of the overflow chamber 16. An orifice 48 in the tape 42 allows communication between the overflow chamber 16 and the sample holding chamber (20 in FIG. 2). The orifice may be circular, rectangular, or irregular in shape. The overflow chamber is constructed in the form of a low box. An air tube 18 delivers air from the pump 36 (not shown in FIG. 5) to the overflow chamber 16. The volume of the overflow chamber is in the range of 0.2 microliters to 1 milliliter. A preferred volume of the overflow chamber is in the range of 1 microliter to 10 microliters. The diameter of the circular orifice is from about 100 microns to about 1000 microns.

Movement of sample. In FIG. 2, a metered sample is forced from the sample holding chamber 20 through the pre-sensor channel 24 into the analysis location 31 as the plunger in the analyzer compresses the cartridge air bladder 36 and forces air through the air pipe 18 into the overflow chamber 16 and through the orifice (48 in FIG. 5). As the sample moves through the dry conduits, it is necessary that the fluid front wet the walls of the channels uniformly. If the surface energy of the conduit is not equal on all sides, uneven flow may occur, causing the formation of air bubbles within the segment. The surfaces of the channel within the cover, the adhesive gasket, the reagent coating, and the chips must therefore be of equivalent surface energy. Surface treatments of the components are needed to assure this uniformity.

Reagent. It is well known in the art to place dried reagent in a fluid path for reaction with a sample to be assayed. A variety of components are included in the reagent, some of which contribute to the rapid redissolving of the dried reagent by the fluid sample. These include a water-soluble polymer, gelatin, agarose, a polysaccharide, polyethylene glycol, polyglycine, a saccharide, sucrose, an amino acid, glycine, a buffer salt, sodium phosphate, HEPES buffer, and a dye molecule.

It is known in the art to include a material for inducing coagulation via the extrensic pathway (60 in FIG. 9). Material suitable for this use with the cartridge of this invention include celite, kaolin, diatomaceous earth, clay, silicon dioxide, ellagic acid, natural thromboplastin, recombinant thromboplastin, phospholipid, and mixtures thereof. A preferred inducer is celite.

Thrombin-substrate Reaction. The substrate used in the electrogenic assay has an amide linkage that mimics the thrombin-cleaved amide linkage in fibrinogen. Specifically, the substrate is a tosyl-glycyl-prolinyl-arginyl-, H-D-phenylalanyl-pipecolyl-, or benzyl-phenylalanyl-valyl-arginyl- moiety attached to an N-phenyl-p-phenylenediamine or N-[p-methoxyphenyl-]-p-phenylenediamine moiety. Thrombin cleaves the amide bond at the carboxy-terminus of the arginine residue or pipecolyl residue because the bond structurally resembles the thrombin-cleaved amide linkage in fibrinogen. The product of the thrombin-substrate reaction is the electrochemically inert tosyl-glycyl-prolinyl-arginyl-, H-D-phenylalanyl-pipecolyl-, or benzyl-phenylalanyl-valyl-arginyl- and the electroactive compounds N-phenyl-p-phenylenediamine or N-[p-methoxyphenyl-]-p-phenylenediamine. The tripeptide sequence was chosen because it renders the substrate virtually non-reactive with blood proteases other than thrombin and the reactivity of thrombin with the arginine amide linkage in the molecule is very similar to its reactivity with the target amide linkage in fibrinogen. When the substrate is present in a blood or blood derivative sample, generated thrombin simultaneously converts it and fibrinogen to their cleavage products. The electrochemical species reaction product is detected by an electrochemical sensor.

There are a wide variety of suitable electrogenic materials which exhibit reversible or quasi-reversible electrochemical reactions known in the art which may be assayed using an amperometric sensor of this invention. For example, ferrocene, ferrocyanide, and other organometallic species may be detected. Others include phenazine derivatives. Any suitable electrogenic material may be combined with a suitable substrate for use in assaying an enzyme. For example, suitable electrogenic materials may be combined with a suitable tripeptide with an arginine residue for use in determining the presence of thrombin.

An indicator electrogenic material which is detected at a potential different from the fu detection potential for the substrate or the electrogenic product of the enzymatic reaction may be included in the reagent. Such a second electrogenic material is useful for standardizing the amperometric sensor. Suitable electrogenic materials for this purpose include ferrocene, ferrocyanide, and other organometallic species, phenazine derivatives, N-phenyl-p-phenylenediamine and N-[p-methoxyphenyl-]-p-phenylenediamine.

The test is termed "electrogenic" because the electrochemically detectable species is generated to allow determination of a rate measurement or the test endpoint. This is similar to "chromogenic" or "fluorogenic" endpoint tests in which a change in the light absorbing or emitting properties of a sample indicates the rate measurement or endpoint. In a chromogenic test, for example, the cleaved portion of the substrate molecule is colorless when attached to the tripeptide and brightly colored when liberated by the action of thrombin. By monitoring the wavelength at which the free species absorbs light, the time at which active thrombin is produced can be determined, chromogenic APTT and PT tests have been shown to have good correlation to traditional APTT and PT plasma tests.

The cartridge of this invention is not limited only to the assay of coagulation enzymes. Assays can be devised for a variety of enzymes, such as glucose oxidase, lactate oxidase, and other oxidoreductases, dehydrogenase based enzymes, and alkaline phosphatase and other phosphatases, and serine proteases. Other enzymes known in the art to be assayed in clinical chemical procedures can be assayed with this invention.

Reagent Mixing. Once in the analysis location, the sample must be mixed with the reagent. For these tests, it is required that the reagent is homogeneously distributed throughout the sample in the region of the sensor within a few seconds of the start of dissolution.

In the coagulation cartridge, the clot reaction is initiated in a specific region of the sensor channel over the sensor chips. A length of the wall within the channel is coated with the reagent, as indicated at 30 FIG. 2 and FIGS. 6A–C. Oscillating a segment of the sample over the reagent induces convection. The motion is controlled so that the trailing edge of the blood segment continually moves back and forth across the reagent coating, as depicted in FIGS. 6A–C.

Figure 6A:
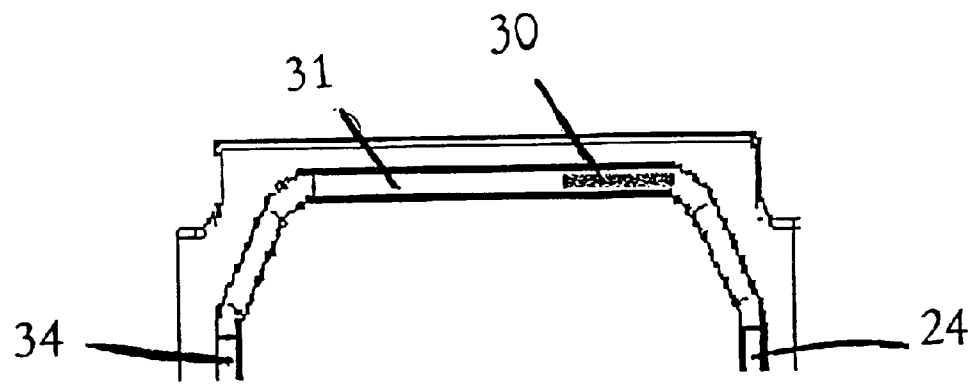
FIGS. 6A, 6B, and 6C show the oscillation of sample in the analysis location.
Figure 6B:
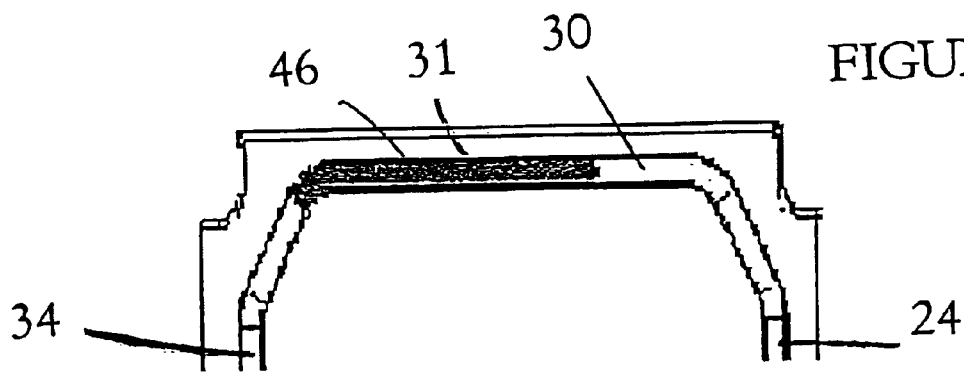
Figure 6C:
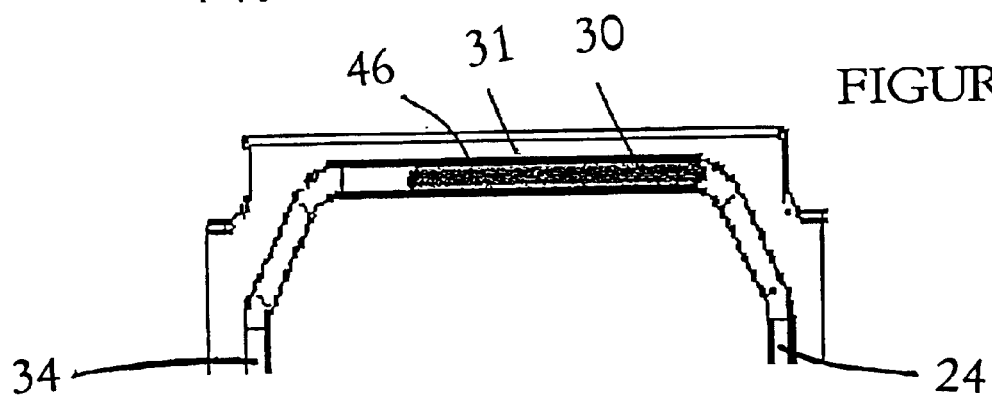

FIGS. 6A–C show the analysis location 31 along with other portions of the fluid path pre-sensor channel 24 and waste tube 34. The dried reagent deposit 30 is shown in the analysis location 31. FIG. 6B shows a sample 46 which has been moved past the reagent deposit. FIG. 6C shows the sample 46 after it has been oscillated back over the area where in the reagent was deposited. Although the reagent 30 is shown deposited in the analysis location 31 in FIG. 6A, it is possible to place the reagent deposit at more than one site in the analysis location, and reagent deposits may be placed at any location in the entire fluid path (38 in FIG. 2).

The oscillation is maintained using a fluid position sensor coincident with the reagent coating. This sensor comprises the two parallel bars on the sensor chip shown in FIG. 6. FIG. 6 shows the conductimetric sensors 28. These sensors 28 lie perpendicular to the length of the sensor channel and the electrical resistance between them is used to monitor the relative position of the fluid front. At the extremes, an open circuit reading indicates that the fluid has been pushed off the sensor and a closed circuit reading indicates the sensor is covered with sample. The fluid is continually moved forward and back at a controlled velocity. Controlling the time for which the sensor remains open and closed circuit controls the position at which the fluid changes direction.

In a preferred method, the pneumatic pump oscillates the sample in the analysis chamber with the trailing edge of the sample positioned in the region of the conductivity sensor in order to dissolve the substrate in that portion of the sample near the trailing edge. The oscillation may be at a frequency in the range of 0.2 to 10 Hertz for a period in the range of 1 to 100 seconds. In a preferred method, the oscillation is at a frequency in the range of about 1.5 Hertz for a period of about 20 seconds. In another preferred method the oscillation is at a frequency of about 0.3 Hertz and the amperometric or second sensor generates a signal at each oscillation. If erythrocytes are present in the fluid sample, the oscillation is at a frequency adequate to prevent the settling of erythrocytes on the sensor. In a preferred method, the amperometric sensor determines the concentration of the product each time the sample is oscillated past the amperometric sensor.

In a preferred embodiment, the first amperometric sensor signal is stored by the analyzer and subsequent signals from the amperometric sensor are stored and are compared to the first and other stored signals in order to determine the maximum rate of change in the amperometric sensor signal. These data are analyzed to determine a fixed fraction of the maximum rate of change of the amperometric sensor signal. These data are used to determine the coagulation parameter of interest.

Figure 7:
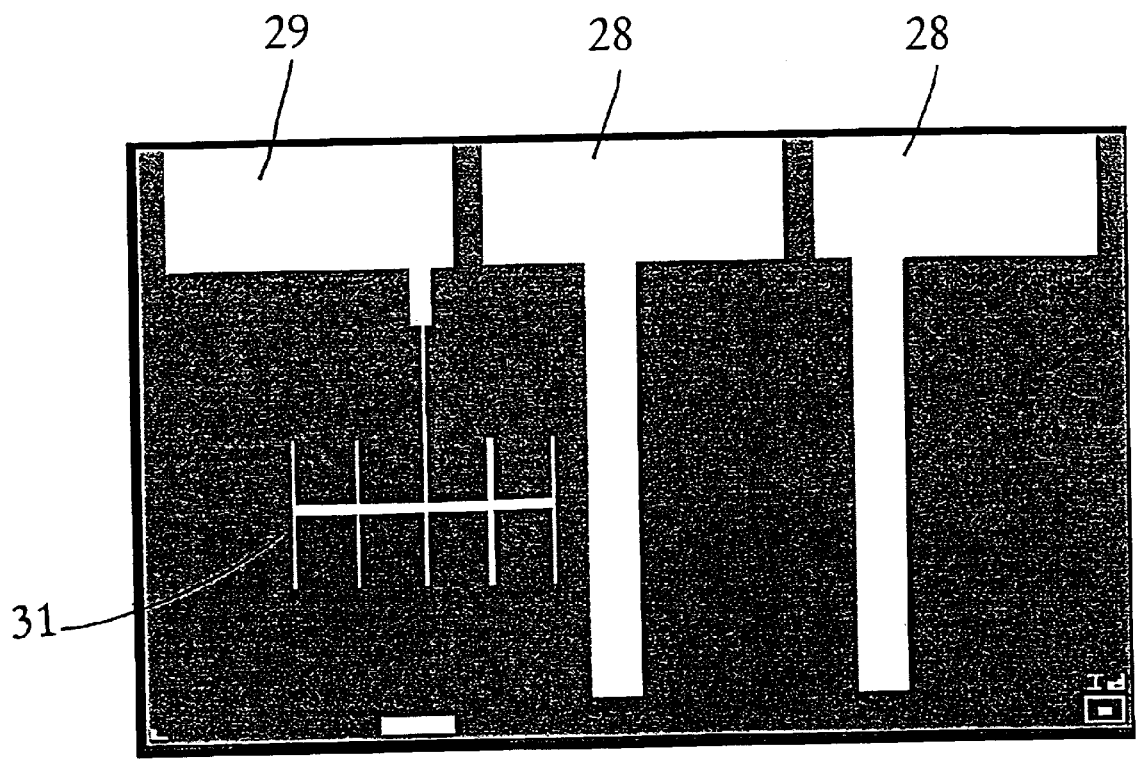
FIG. 7 shows the conductimetric and amperometric sensors of the cartridge.

FIG. 7 also shows the amperometric sensor 29 in which the sensing portion is in the form of an antenna 31.

Although the sensor in the example in FIG. 7 is an amperometric sensor, other electrochemical processes which use other electrochemical sensors can be used. For example, a potentiometric sensor may be used to detect ion species such as $Na^+$ and $K^+$.

In the preferred embodiment of the present invention the analyzer applies a potential to a amperometric sensor at with the generation of an electrochemical signal, said signal being proportional to the concentration of the product in the fluid sample. The amperometric sensor has an applied potential of approximately +0.4 V versus a silver-silver chloride electrode and, in another preferred embodiment, the amperometric sensor has an applied potential of approximately +0.1 V versus a silver-silver chloride electrode. The signal generated by the enzyme reaction product at approximately +0.1V is distinguishable from the signal generated by the unreacted substrate at approximately +0.4 V.

In the embodiments of the invention which use the substrates tosyl-glycyl-prolinyl-arginyl-, H-D-phenylalanyl-pipecolyl-, or benzyl-phenylalanyl-valyl-arginyl- moiety attached to an N-phenyl-p-phenylenediamine or N-[p-methoxyphenyl-]-p-phenylenediamine moiety, the intact substrates are detected at a voltage of approximately +0.4V. The electrogenic reaction products N-phenyl-p-phenylenediamine or N-[p-methoxyphenyl-]-p-phenylenediamine are detected at a voltage of approximately +0.1V. Thus in these embodiments, the analyzer applies a potential to a amperometric sensor with the generation of an electrochemical signal which is proportional to the concentration of the substrate in the fluid sample. Also, the analyzer applies a potential to a amperometric sensor with the generation of an electrochemical signal which is proportional to the concentration of the product in the fluid sample. After hydrolysis of the substrate by thrombin, a product is formed which reacts at the amperometric sensor with the generation of a signal distinguishable from the signal generated by the substrate.

It should be noted that the exact voltages used to amperometrically detect the substrate and the product will vary depending on the chemical structure of the substrate and product. It is important that the difference in the voltages used to detect the substrate and the product be great enough to prevent interference between the readings. With some substrates, the voltage required to electrochemically detect the substrate is so high as to beyond practical measurement. In these cases, it is only necessary that the product be detectable amperometrically.

The sensors are preferably microfabricated of any suitable electroconductive material and are preferably made of gold, platinum, silver or iridium. The methods for patterning metals on silicon wafers are well known in the art. It is also desirable to coat the sensor with a thin organic layer which prevents poisoning of the sensor surface by blood components such as a self-assembled thiol film, as is known in the art. Mercaptoalkanols form self-assembled thiol firms, and some examples include mercaptoethanol, mercaptopropanol, mercaptobutanol, and mixtures thereof.

Figure 8:
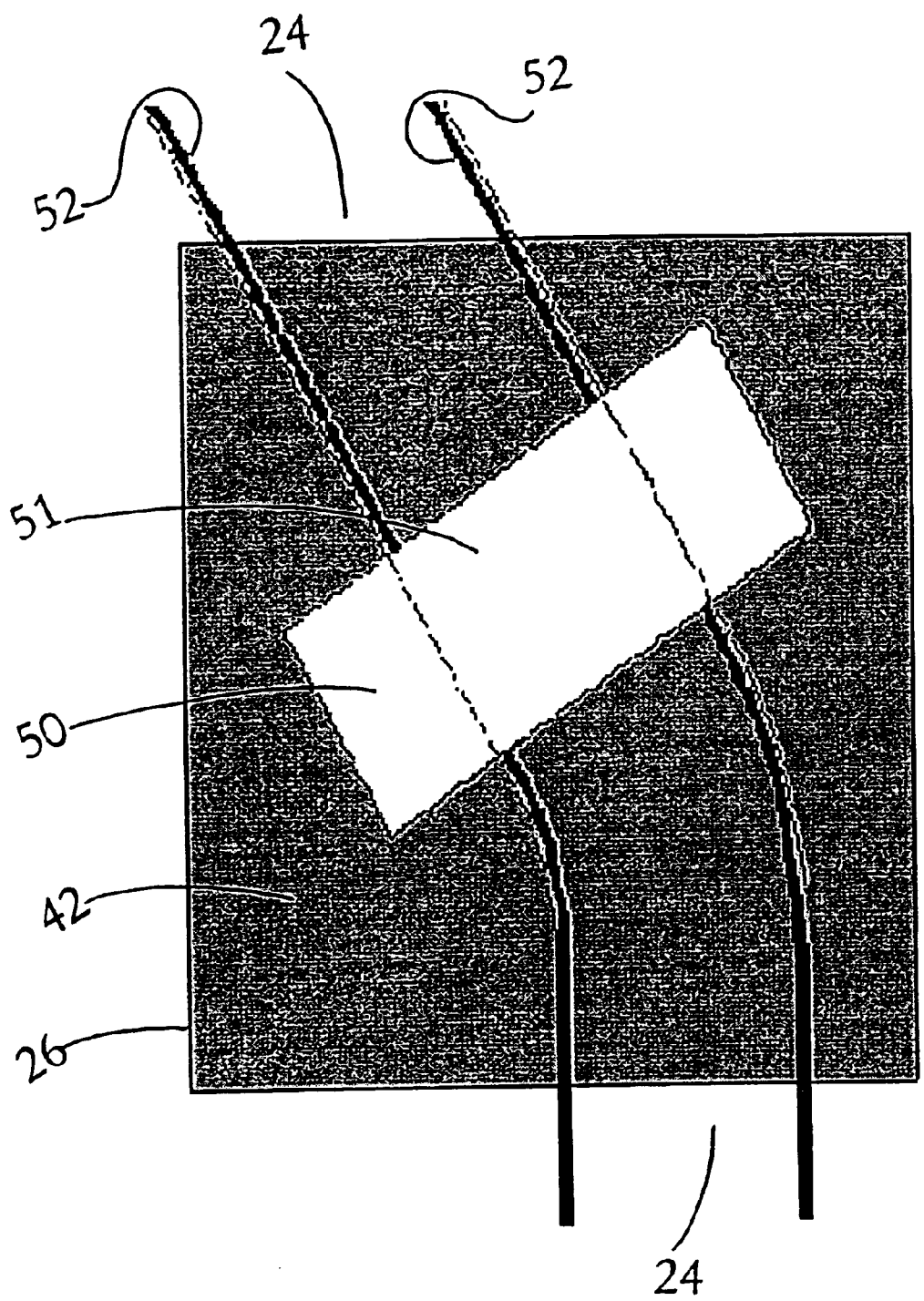
FIG. 8 shows the hydrophobic chip in the fluid path.

FIG. 8 is a plot of the distance from the end of the sample segment in mm along the abscissa versus the concentration of dissolved reagent in micro moles along the ordinate. A diagram at the top of FIG. 8 shows a fluid sample 46, conductimetric sensors 28, and amperometric sensor 30. The data points of FIG. 8 indicate the concentration of dissolved reagent along the length of the column of fluid sample.

Mixing in this manner produces a concentration gradient along the length of the blood segment. As shown in FIG. 8, the concentration is highest at the edge of the segment that was swept across the reagent and decreases toward the center of the fluid columm. In FIG. 8 the measured concentration and the cartridge-to-cartridge variability in the concentration (the error bars show one standard deviation) are plotted as a function of position along the blood segment. At the sensor location, one standard deviation of the reagent concentration is 10% of the mean concentration.

Maintaining the fluid position. In this embodiment the dissolution profile is not uniform, cartridge-to-cartridge reproducibility of the reagent concentration at the sensor depends on both the cartridge-to-cartridge consistency of sample positioning and the ability to maintain quiescence within the sample throughout the course of the test. The former is achieved through active position control using feedback from the same fluid position sensor employed to monitor the mixing oscillation. For short duration tests, the resistance between the bars of the sensor is maintained within a window a set number of ohms above the closed circuit reading. The sample-air interface is therefore held between the two bars. If the sample is drifting back toward the sample-holding chamber, the resistance will decrease until a pre-set limit is triggered causing the analyzer to push the sample forward until the control resistance is again achieved. If the sample drifts towards the cartridge waste tube, the resistance will drift higher causing the analyzer to pull the sample backwards. Because the resistance is a sensitive function of the fluid position, the fluid front can be maintained within 100 microns of a nominal position. The corrective motions do not cause convection within the sample as they are of very low amplitude and speed.

Control to a set resistance is sufficient in tests requiring less than 60 to 100 seconds for completion. Some types of coagulation tests produce results that are always in this range. Other tests, however, require up to 15 minutes before the endpoint is achieved. With extended times, red blood cells may settle and blood components may dry at the exposed chip surface. Both conditions cause the resistance for a given fluid position to increase and interfere with the position controller. In the case of settling, the resistance gradually increases causing the controller to respond as though the fluid has drifted forward. The segment is then pulled backward to maintain the set-point resistance.

To circumvent these problems in tests requiring longer periods of position control, the fluid is periodically moved to the fully closed circuit position and the closed circuit resistance is measured. The fluid is then re-positioned at a resistance value offset relative to the new closed circuit reading. The oscillation continually wets the chip to prevent drying and the offset resistance is set relative to the closed circuit reading for the settled sample. These motions do not cause excessive convection within the sample as they are again of low amplitude and velocity.

Convection occurs within the sample near the sensor if the positioned segment is not fluidically isolated. Any flow path connecting the positioned sample segment with the sample-holding chamber will provide a route by which the sample segment may be siphoned backwards into the holding chamber. This is because the surface energy and surface area to volume ratio of the sample-holding chamber necessary to allow capillary draw also causes the chamber to be preferentially wetted. If this occurs, the motion of fluid siphoning from the tail end of the sample segment causes fluid deeper within the segment to be drawn over the sensor. The reagent concentration in the sample volume around the sensor therefore decreases as it is mixed with sample containing a lower concentration of reagent.

A fluid path which is of sufficiently low resistance to allow this transfer forms at the seam between the cartridge cover and the tape as the sample is pushed through the pre-sensor channel. This is because the radius of the pre-sensor channel edge, which is created during the process of injection molding the cover, when pressed against the tape gasket may form a thin capillary that is filled by blood sheared from the passing segment. Once this capillary is filled, sample may siphon through it back into the sample-holding chamber. To prevent siphoning, the fluid path must be broken. In one embodiment, this is accomplished in the coagulation cartridge by cutting away a section of the tape gasket beneath the pre-sensor channel to expose the surface of a polytetrafluoroethylene chip that is contained within a well in the base. The surface of the chip is flush with the surface of the base. The cutout in the tape undercuts the cover channel so that the capillary formed at the cover-gasket seam is interrupted in the region of the chip. The hydrophobic surface of the polytetrafluoroethylene chip prevents the formation of an alternate pathway along the surface exposed by the opening. This is shown schematically in FIG. 9.

FIG. 9 shows a polytetrafluoroethylene chip 26, located in a well on the base and covered by the tape 42, and a portion of the pre-sensor channel 24. In this portion of the pre-sensor channel 24, the channel is cut into the top or first side of the cartridge and the tape 42 forms the bottom wall of the pre-sensor channel 24. FIG. 9 shows a section 50 where the tape 42 has been cut away exposing a portion 51 of the polytetrafluoroethylene chip 26 to the sample contained in the pre-sensor channel 24. Sample which has entered the capillary region described in the previous paragraph is depicted in FIG. 9 at 52.

The hydrophobic area may be constructed using a number of different materials. It may be a hydrophobic matrix coating such as wax, petroleum gel, and non-polar organic film. The hydrophobic area may be formed of polytetrafluoroethylene, plastic coated with polytetrafluoroethylene, polyimide treated with a fluoride ion-plasma, silicon dioxide coated with an organic compound, an alloy of tungsten and titanium, and silver coated with silver chloride. A preferred hydrophobic area is made of polytetrafluoroethylene.

Prototype cartridges to perform Activated Clotting Time (ACT), Activated Partial Thromboplastin Time (APTT), and Prothrombin Time (PT) tests have been developed and tested. Clinical trials conducted with each cartridge type have demonstrated satisfactory performance with respect to test precision and accuracy. All coagulation tests utilize the same cartridge components and are differentiated by the composition of the dry reagent.

It will be apparent to those skilled in the art that the examples and embodiments described herein are by way of illustration and not of limitation, and that other examples may be utilized without departing from the spirit and scope of the present invention, as set forth in the appended claims.

What we claim is:

1. A cartridge for delivering a fluid sample to an analysis location comprising:
   a housing having a closable sample entry port for receiving a fluid sample;
   a holding chamber having a first end in communication with the entry port, the holding chamber having a second end with a capillary stop; wherein the analysis location is in communication with the capillary stop; and wherein the capillary stop selectively allows passage of the sample from the holding/chamber to the analysis location;
   an overflow chamber in communication with the holding chamber, separated by a holding chamber wall which has an orifice for said communication, for handling overflow of incoming sample; and
   a pump for providing a force to the fluid sample in the holding chamber, thereby allowing passage of the sample through the capillary stop.

2. The cartridge of claim 1 wherein the shape of the orifice is circular.

3. The cartridge of claim 1 wherein the orifice is circular with a diameter of about 100 microns to about 1000 microns.

4. The cartridge of claim 1 wherein the area of the orifice is larger than the area of the capillary stop.

5. The cartridge of claim 1 wherein the orifice has a lower resistance to fluid flow than does the capillary stop.

6. The cartridge of claim 1 wherein a roof of the holding chamber comprises a tape and the orifice comprises a hole in the tape.

7. The cartridge of claim 1 wherein the volume of the holding chamber between the orifice and the capillary stop corresponds substantially to the volume of the fluid sample.

8. The cartridge of claim 7 wherein the overflow chamber receives excess sample from the holding chamber through the orifice.

9. The cartridge of claim 1 further comprising a pre-sensor chamber between the capillary stop and the analysis location.

10. The cartridge of claim 9 wherein the cross-sectional area of the holding chamber is larger than the cross-sectional areas of the pre-sensor chamber and the analysis location.

11. The cartridge of claim 9 further comprising a hydrophobic area between the analysis location and the pre-sensor chamber.

12. The cartridge of claim 11 wherein the hydrophobic area comprises a hydrophobic matrix coating selected from the group consisting of wax, petroleum gel, and non-polar organic film.

13. The cartridge of claim 11 wherein the hydrophobic area comprises a layer of material selected from the group consisting of polytetrafluoroethylene, plastic coated with polytetrafluoroethylene, polyimide treated with a fluoride ion-plasma, silicon dioxide coated with an organic compound, an alloy of tungsten and titanium, and silver coated with silver chloride.

14. The cartridge of claim 11 wherein the hydrophobic area comprises a layer of polytetrafluoroethylene.

15. The cartridge of claim 1 wherein the capillary stop has a rectangular shape wherein the smallest dimension is about 100 microns to about 400 microns.

16. The cartridge of claim 1 wherein the overflow chamber has walls which are wetted when excess sample enters the overflow chamber.

17. The cartridge of claim 1 wherein excess sample is forced into the overflow chamber by closure of the entry port closure.

18. The cartridge of claim 1 wherein the wall surfaces of the holding chamber are corona treated.

19. The cartridge of claim 1 wherein the volume of the sample is in the range of 1 microliter to 1 milliliter.

20. The cartridge of claim 1 wherein the volume of the sample is in the range of 20 microliters to 50 microliters.

21. The cartridge of claim 1 wherein the volume of the overflow chamber is in the range of 0.2 microliters to 1 milliliter.

22. The cartridge of claim 1 wherein the volume of the overflow chamber is in the range of 1 microliter to 10 microliters.

23. The cartridge of claim 1 wherein the pump is in fluidic connection with the overflow chamber.

24. The cartridge of claim 1 wherein the force provided to the sample is a pneumatic force.

25. The cartridge of claim 1 which includes an upper housing, a lower housing, and a film coated on both sides with adhesive, the film interposed between the upper housing and the lower housing.

26. The cartridge of claim 1 wherein the holding chamber or the overflow chamber or both, or portions thereof, are treated to impart a high energy surface to the interior chamber surfaces.

27. The cartridge of claim 1 adapted for use with an analyzer.

28. The cartridge of claim 27 wherein the pump is actuated by an actuator element of the analyzer.

29. The cartridge of claim 1 further comprising a predetermined amount of reagent in the analysis location for mixing with the fluid sample.

30. The cartridge of claim 1 further comprising a circumferential well around the entry port for receiving spilled fluid sample.

31. The cartridge of claim 1 wherein the interior surfaces of the holding chamber and or the overflow chamber are corona treated.

32. The cartridge of claim 1 wherein the holding chamber has a lower interior surface to volume ratio than does the overflow chamber.

33. The cartridge of claim 1 wherein the entry port closure makes an air-tight seal when closed.

34. The cartridge of claim 1 further comprising a predetermined amount of reagent in the holding chamber for mixing with the sample.

35. The cartridge of claim 1 further comprising at least one sensor.

36. The cartridge of claim 1 in which the analysis location comprises at least one sensor.

37. A method of assaying an enzyme in a sample of blood or blood derivative, comprising the steps of:
introducing the sample into a cartridge of claim 1 which includes an analysis location,
metering a portion of the sample,
moving the metered sample to the analysis location,
mixing the metered sample with reagent at the analysis location,
allowing the enzyme to react with the reagent,
positioning the reacted sample at a sensor, and
detecting the product of the enzyme reaction using the sensor.

38. A cartridge adapted for use with an analyzer for assaying an enzyme in a fluid sample comprising:
a housing having a sample entry port, overflow chamber, holding chamber, and an analysis location containing a hydrophobic area in part,
an airtight entry port closure,
a pump actuated by the analyzer for moving the sample within the cartridge,
one or more reagent deposits in the analysis location comprising at least one substrate capable of reaction with an enzyme in the fluid sample, the reaction of the enzyme forming a detectable reaction product,
a first sensor for detecting the location of the fluid sample, and
a second sensor for detecting the detectable reaction product.

39. The cartridge of claim 38 wherein the reaction product is detected by an optical sensor.

40. The cartridge of claim 38 wherein the reaction product is an electrochemical species detected by an electrochemical sensor.

41. The cartridge of claim 38 wherein the enzyme is selected from the group consisting of factor VII, factor VIII, factor IX, factor X, factor XI, factor XII, and thrombin.

42. The cartridge of claim 38 wherein the enzyme is thrombin.

43. The cartridge of claim 38 wherein the reagent includes solubility-enhancing components.

44. The cartridge of claim 38 wherein the volume of the fluid sample delivered to the analysis location is metered.

45. The cartridge of claim 38 wherein the reagent includes an electrochemical species other than the substrate and its reaction product.

46. The cartridge of claim 45 wherein the electrochemical species is detectable at a different electrical potential than the substrate and the product.

47. The cartridge of claim 38 wherein substrate or reagent is deposited at more than one site within the analysis location.

48. The cartridge of claim 38 wherein the fluid sample is oscillated past the first and second sensors while in the analysis location.

49. The cartridge of claim 48 wherein the second sensor measures the concentration of reaction product each time the fluid sample is oscillated past the second sensor.

50. The cartridge of claim 38 wherein the reagent comprises a matrix that promotes rapid dissolution into the fluid sample.

51. The cartridge of claim 38 wherein the reagent comprises one or more components selected from the group consisting of a water-soluble polymer, gelatin, agarose, a polysaccharide, polyethylene glycol, polyglycine, a saccharide, sucrose, an amino acid, glycine, a buffer salt, sodium phosphate, HEPES buffer, and a dye molecule.

52. The cartridge of claim 38 further comprising a reagent that promotes the coagulation of blood or a blood derivative.

53. The cartridge of claim 52 wherein the reagent is selected from the group consisting of celite, kaolin, diatomaceous earth, clay, silicon dioxide, ellagic acid, natural thromboplastin, recombinant thromboplastin, phospholipid, and mixtures thereof.

54. The cartridge of claim 38 wherein the first sensor is a conductimetric sensor and the second sensor is an amperometric sensor.

55. The cartridge of claim 54 wherein the analyzer applies a potential to an amperometric sensor with the generation of an electrochemical signal, said signal being proportional to the concentration of the substrate in the fluid sample.

56. The cartridge of claim 54 wherein the analyzer applies a potential to a amperometric sensor with the generation of an electrochemical signal, said signal being proportional to the concentration of the product in the fluid sample.

57. The cartridge of claim 54 wherein hydrolysis of the substrate by thrombin forms a product which reacts at the amperometric sensor with the generation of a signal distinguishable from a signal generated by the substrate.

58. The cartridge of claim 54 wherein the amperometric sensor is microfabricated.

59. The cartridge of claim 54 wherein the conductimetric sensor is microfabricated.

60. The cartridge of claim 54 wherein said amperometric sensor has an applied potential of approximately +0.4V versus a silver-silver chloride electrode.

61. The cartridge of claim 54 wherein said amperometric sensor has an applied potential of approximately +0.1V versus a silver-silver chloride electrode.

62. The cartridge of claim 54 wherein said conductimetric sensor is proximal to the capillary stop and said amperometric sensor is distal from the capillary stop.

63. The cartridge of claim 38 wherein said first or said second sensor is comprised of a metal selected from the group consisting of gold, platinum, silver, and iridium.

64. The cartridge of claim 38 wherein said first or said second sensor is coated with a self-assembled thiol film.

65. The cartridge of claim 38 wherein said first or said second sensor is in the shape of an antenna.

66. The cartridge of claim 38 wherein the reagent includes a substance that promotes coagulation of blood.

67. The cartridge of claim 38 wherein the fluid sample is blood or a blood derivative.

68. The cartridge of claim 67 wherein the blood derivative is selected from the group consisting of blood containing an additive or diluent, plasma, serum and plasma or serum containing an additive or diluent.

69. The cartridge of claim 38 wherein the substrate is selected from the group consisting of a tosyl-glycyl-prolinyl-arginyl-, H-D-phenylalanyl-pipecolyl-, and benzyl phenylalanyl-valyl-arginyl- moiety attached to a moiety selected from the group consisting of an N-phenyl-p-phenylenediamine, and an N-[p-methoxyphenyl-]-p-phenylenediamine moiety.

70. The cartridge of claim 38 wherein the reaction product is selected from the group consisting of N-phenyl-p-phenylenediamine and N-[p-methoxyphenyl-]-p-phenylenediamine moiety.

71. The cartridge of claim 38 wherein the enzyme is selected from the group consisting of glucose oxidase, lactate oxidase, and other oxidoreductases, dehydrogenase based enzymes, alkaline phosphatase and other phosphatases, and serine proteases.

72. The cartridge of claim 38 wherein a sensor is coated with a mercaptoalkanol reagent selected from the group consisting of mercaptoethanol, mercaptopropanol, mercaptobutanol, and mixtures thereof.

73. The cartridge of claim 38 wherein a reagent deposit is in the path of the moving fluid sample.

74. A method of assaying an enzyme in a sample of blood or blood derivative comprising the steps of:
obtaining a sample of blood or blood derivative,
placing the sample into the entry port of a cartridge of claim 38,
closing the entry port,
activating the pump, thereby forcing a sample from the sample chamber into the analysis chamber,
oscillating the sample back and forth in the analysis chamber, and
determining the concentration of the reaction product using the second sensor.

75. The method of claim 74 wherein the pump oscillates the sample in the analysis chamber with the trailing edge of the sample positioned in the region of a selected sensor in order to dissolve the substrate in that portion of the sample near the trailing edge.

76. The method of claim 74 wherein the oscillation is at a frequency in the range of 0.2 to 10 Hertz for a period in the range of 1 to 100 seconds.

77. The method of claims 74 wherein the oscillation is at a frequency in the range of about 1.5 Hertz for a period of about 20 seconds.

78. The method of claim 74 wherein the oscillation is at a frequency of about 0.3 Hertz and the second sensor generates a signal at each oscillation.

79. The method of claim 74 wherein the oscillation is at a frequency sufficient to prevent settling of erythrocytes on a sensor.

80. The method of claim 74 further comprising the step of:
storing an amperometric first sensor signal after a reagent is dissolved.

81. The method of claim 80 further comprising the step of:
analyzing subsequent amperometric sensor signals to determine the maximum rate of change in sensor signal.

82. The method of claim 81 further comprising the step of:
determining a fixed fraction of the maximum rate of change in the sensor signal.

83. The method of claim 81 further comprising the step of:
determining the coagulation parameter from the first sensor signal and the fixed fraction.

84. A single-use cartridge used in combination with an analyzer for determining a coagulation parameter of a sample of blood or blood derivative, comprising;
a cartridge which includes an entry port for receiving a sample, an entry port closure, a holding chamber in communication at a first end with the entry port, and a capillary stop in communication with the holding chamber at a second end, the capillary stop also in communication with an analysis chamber,
the holding chamber in communication with an overflow chamber for receiving and retaining excess sample,
the overflow chamber in communication with a pneumatic pump actuated by the analyzer,
the analyzer actuating the pneumatic pump to displace sample in the holding chamber through the capillary stop into the analysis chamber to deliver a metered portion of the sample into the analysis chamber,
the analysis chamber containing a substrate for the enzyme thrombin capable of dissolving in the metered sample, an amperometric sensor for detecting the product of the reaction between thrombin and the substrate, and a conductimetric sensor for detecting the position of the sample in the analysis chamber,
the amperometric sensor and the conductimetric sensor connected to the analyzer for providing output signals to the analyzer,
the analyzer capable of using the output signal of the conductimetric sensor to actuate the pneumatic pump to control the position of the sample in the analysis chamber,
the analyzer capable of determining the coagulation parameter from the output signal of the amperometric sensor, and the cartridge containing a hydrophobic area between the capillary stop and the analysis chamber to prevent sample in the analysis chamber from being drawn back into the holding chamber.

85. A cartridge for delivering a fluid sample to an analysis location comprising: a housing having a closable sample entry port for receiving a fluid sample; a holding chamber having a first end in communication with the entry port, the holding chamber having a second end with a capillary stop;

wherein the analysis location is in communication with the capillary stop and comprising a pre-sensor chamber between the capillary stop and the analysis location, further comprising a hydrophobic area between the analysis location and the pre-sensor chamber; and wherein the capillary stop selectively allows passage of the sample from the holding chamber to the analysis location;

an overflow chamber, in communication with the holding chamber for handling overflow of incoming sample; and a pump for providing a force to the fluid sample in the holding chamber, thereby allowing passage of the sample through the capillary stop.

86. A cartridge for delivering a fluid sample to an analysis location comprising: a housing having a closable sample entry port for receiving a fluid sample; a holding chamber having a first end in communication with the entry port, the holding chamber having a second end with a capillary stop; wherein the analysis location is in communication with the capillary stop; and wherein the capillary stop selectively allows passage of the sample from the holding chamber to the analysis location;

an overflow chamber in communication with the holding chamber, for handling overflow of incoming sample; and a pump in fluidic connection with the overflow chamber for providing a force to the fluid sample in the holding chamber, thereby allowing passage of the sample through the capillary stop.

87. The cartridge of claim 86 further comprising a pre-sensor chamber between the capillary stop and the analysis location.

88. The cartridge of claim 86 wherein the cross-sectional area of the holding chamber is larger than the cross-sectional areas of the pre-sensor chamber and the analysis location.

89. The cartridge of claim 86 further comprising a hydrophobic area between the analysis location and the pre-sensor chamber.

90. The cartridge of claim 89 wherein the hydrophobic area comprises a layer of polytetrafluoroethylene.

91. The cartridge of claim 86 wherein the wall surfaces of the holding chamber are corona treated.

92. The cartridge of claim 86 wherein the volume of the sample is in the range of 1 microliter to 1 milliliter.

93. The cartridge of claim 86 adapted for use with an analyzer.

94. The cartridge of claim 86 wherein the pump is actuated by an actuator element of the analyzer.

95. The cartridge of claim 86 further comprising a pre-determined amount of reagent in the analysis location for mixing with the fluid sample.

96. The cartridge of claim 86 further comprising at least one sensor.

97. A cartridge for delivering a fluid sample to an analysis location comprising:

a housing having a closable sample entry port for receiving a fluid sample;

a holding chamber having a first end in communication with the entry port, the holding chamber having a second end with a capillary stop; wherein the analysis location is in communication with the capillary stop; and wherein the capillary stop selectively allows passage of the sample from the holding chamber to the analysis location;

an overflow chamber in communication with the holding chamber which is above and in fluid communication with the holding chamber and separated by a holding chamber wall, for handling overflow of incoming sample; and a pump for providing a force to the fluid sample in the holding chamber, thereby allowing passage of the sample through the capillary stop.

98. The cartridge of claim 97 further comprising a pre-sensor chamber between the capillary stop and the analysis location.

99. The cartridge of claim 97 wherein the cross-sectional area of the holding chamber is larger than the cross-sectional areas of the pre-sensor chamber and the analysis location.

100. The cartridge of claim 97 further comprising a hydrophobic area between the analysis location and the pre-sensor chamber.

101. The cartridge of claim 100 wherein the hydrophobic area comprises a layer of polytetrafluoroethylene.

102. The cartridge of claim 97 wherein the wall surfaces of the holding chamber are corona treated.

103. The cartridge of claim 97 wherein the volume of the sample is in the range of 1 microliter to 1 milliliter.

104. The cartridge of claim 97 adapted for use with an analyzer.

105. The cartridge of claim 97 wherein the pump is actuated by an actuator element of the analyzer.

106. The cartridge of claim 97 further comprising a predetermined amount of reagent in the analysis location for mixing with the fluid sample.

107. The cartridge of claim 97 further comprising at least one sensor.

* * * * *